United States Patent [19]
Hutchison

[11] 3,954,110
[45] May 4, 1976

[54] RETENTION CATHETER WITH BILOBATE BALLOON

[76] Inventor: Ernest L. Hutchison, No. 5 Southern Pines Drive, Pine Bluff, Ark. 71601

[22] Filed: Jan. 24, 1974

[21] Appl. No.: 436,232

[52] U.S. Cl. .............................. 128/349 B; 128/246
[51] Int. Cl.² ........................................ A61M 25/00
[58] Field of Search ............ 128/348, 349 R, 349 B, 128/349 BV, 350 R, 351, 344, 325, 246

[56] References Cited
UNITED STATES PATENTS

| | | | |
|---|---|---|---|
| 1,922,084 | 8/1933 | Gerow | 128/349 B |
| 2,919,697 | 1/1960 | Kim | 128/349 B |
| 3,438,375 | 4/1969 | Ericson | 128/349 B |
| 3,630,206 | 12/1971 | Gingold | 128/349 B |
| 3,811,448 | 5/1974 | Morton | 128/349 B |
| 3,889,686 | 6/1975 | Duturbure | 128/349 B |

Primary Examiner—Dalton L. Truluck
Attorney, Agent, or Firm—Ralph R. Pittman

[57] ABSTRACT

A retention catheter, particularly adapted for draining a bodily viscus or cavity, has a bilobated balloon disposed to enclose the distal tip and a pair of opposed drainage eyes retracted from the distal end, the eyes opening through the exteriorly mounted balloon into the drainage lumen. When suitably inflated, the catheter assumes the correct position to enable continuously complete drainage of the cavity from its lowermost portion. A reinforced tip permits use of a wire guide for catheter insertion when this is needed in difficult situations.

3 Claims, 5 Drawing Figures

RETENTION CATHETER WITH BILOBATE BALLOON

BACKGROUND

A majority of the prior art disclosures relating to retention catheters are improvements or modifications of the well known and widely used Foley catheter, all of which, in use, interpose a balloon between the lowermost portion of an associated bladder and a drainage eye at the distal tip.

Other prior art includes catheters having interiorly disposed balloons, the inflation thereof either moving a portion of the enclosed balloon to an exterior position or expanding the end portion of the catheter; the inflation of the balloon in each of these structures causing the appearance of drainage openings into the drainage lumen of the catheters.

Catheters having tips extending beyond the balloon often cause trauma from pressure of the tip, thus creating an area of inflammation which on subsequent cystoscopy may require biopsy for assurance that no malignancy is present. Also, there is always the hazard of the protruding tip causing disruption of suture lines such as those following surgery on the bladder. Further, the drainage eyes, being normally positioned above the lowermost space of the cavity, are not in position to enable complete drainage. The undrained fluid becomes stagnant, encouraging infection, pain and delayed healing.

An important consideration in the construction of any inflatable balloon catheter is the provision of means for monitoring the position of the balloon with respect to the passageway leading to the cavity to be drained, to avoid the hazard attending the inflation of the balloon within the passageway, e.g., the urethral canal. Previously described catheters having drainage eyes at the tip and associated retracted balloons are obviously susceptible to such hazardous procedures; this is also true of catheters having retracted drainage eyes which are caused to appear in response to the inflation of an associated balloon.

SUMMARY OF THE INVENTION

The present invention is concerned only with a particular construction of the distal end portion of a balloon-type catheter, in which the wall thickness is internally increased therealong, an inflatable bilobated balloon is sheathed over the distal end portion of the catheter drainage tube and a pair of opposed drainage eyes register with arch-shaped openings through the balloon wall between the lobes of the inflated balloon, the eyes extending distally from the lower or proximal margin of the balloon.

An inflation channel, small relative to the size of the drainage lumen, extends longitudinally along the interior wall of the drainage lumen from the proximal end of the catheter, in communication with the balloon by means of an aperture through the wall of the drainage tube.

The balloon is attached to the distal end portion of the catheter at the distal tip, and also attached along the entire proximal margin, which includes attachment along the edges of the arch-shaped openings in the balloon wall which register with the drainage eyes, those portions of the balloon lying between the drainage eyes defining a pair of lobes when the balloon is inflated.

Since no part of the balloon is disposed proximally beyond the drainage eyes, the desired retention position of the catheter within a body cavity is indicated by the appearance of liquid at the proximal end of the catheter as the distal end enters a cavity to be drained. The inflation of the balloon may then proceed with assurance that no part of the balloon will be distended within the body passageway leading to the body cavity, and with the further assurance that the drainage eyes remain unobstructed between the lobes of the balloon and at the juncture of the body passageway with the body cavity.

The foregoing procedure enables continuous drainage of fluid from the lowermost space of the body cavity, precluding the collection of a residual pool formed by incomplete drainage. Following surgery involving the bladder, incomplete drainage encourages infection and spasm along with delay in convalescence; in nonsurgical cases, inflammation appearing in the bladder as a result of pressure from the protruding tip of previously designed catheters may require biopsy upon subsequent cystoscopy in order to determine if malignancy is present.

BRIEF DESCRIPTION OF THE DRAWING

The several figures of the drawing are enlarged to more clearly illustrate the invention; the sections are shown as rubber, a satisfactory material; however, there are available other suitable materials, e.g., plastic elastomers.

DESCRIPTION OF THE PREFERRED EMBODIMENT

Figure 1:
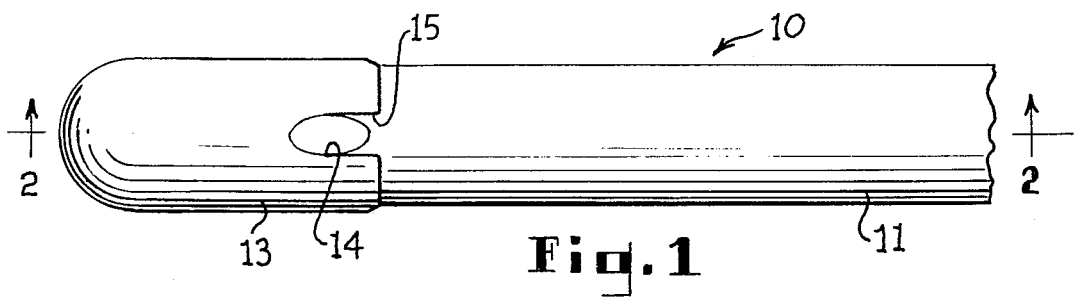
FIG. 1 is a side elevation of the invention, in the normally undistended condition.
Figure 2:
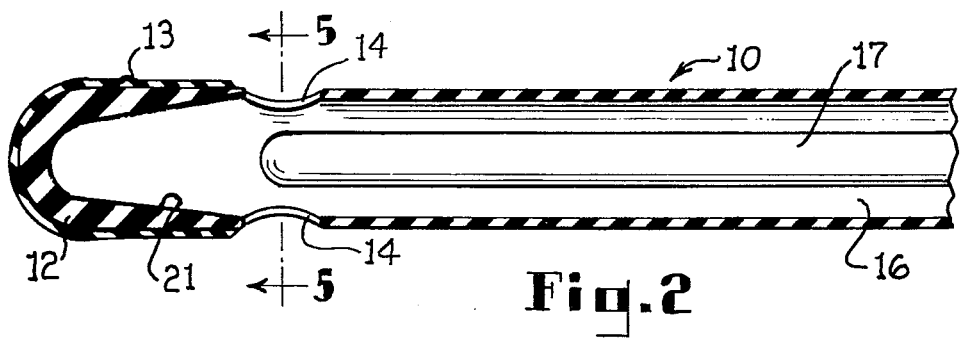
FIG. 2 is a sectional view along the line 2 — 2 of FIG. 1.
Figure 5:
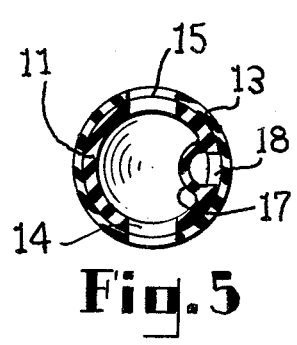
FIG. 5 is a sectional view along the line 5 — 5 of FIG. 2.

Referring to FIGS. 1, 2, and 5 of the drawing, the catheter 10 has an elongate tubular body portion 11 defining the drainage lumen 16. The distal end of the catheter is closed by the reinforced tip portion 12. To facilitate the insertion of the catheter in difficult cases, the reinforced tip portion 12, housing the conically tapered recess 21, allows the use of a wire catheter guide as is commonly done with previously designed catheters. The recess 21 is a coaxial extension of the drainage lumen 16.

A pair of diametrically opposed drainage eyes are apertured through the wall of the body portion 11 at the distal end of the drainage lumen, which terminates at the base of the conical recess 21. A generally thimble-shaped balloon 13 is sheathed over the tip portion 12 and cemented thereto (a) at a spot on the extreme distal tip; (b) along the marginal edge of the balloon which curves around the body portion 11 and (c) along the marginal edge of the arch-shaped openings 15, the latter being disposed to register with the drainage eyes 14.

A relatively small tubular inflation channel 17 extends along the inner surface of the drainage lumen 16 from the proximal end of the catheter to the end of the drainage lumen, at which location the inflation lumen communicates with the balloon 13 through the aperture 18 (FIG. 5) in the wall of the tubular body portion 11. The foregoing describes an inflation lumen construction commonly used in many currently available balloon catheters.

Figures 3, 4:
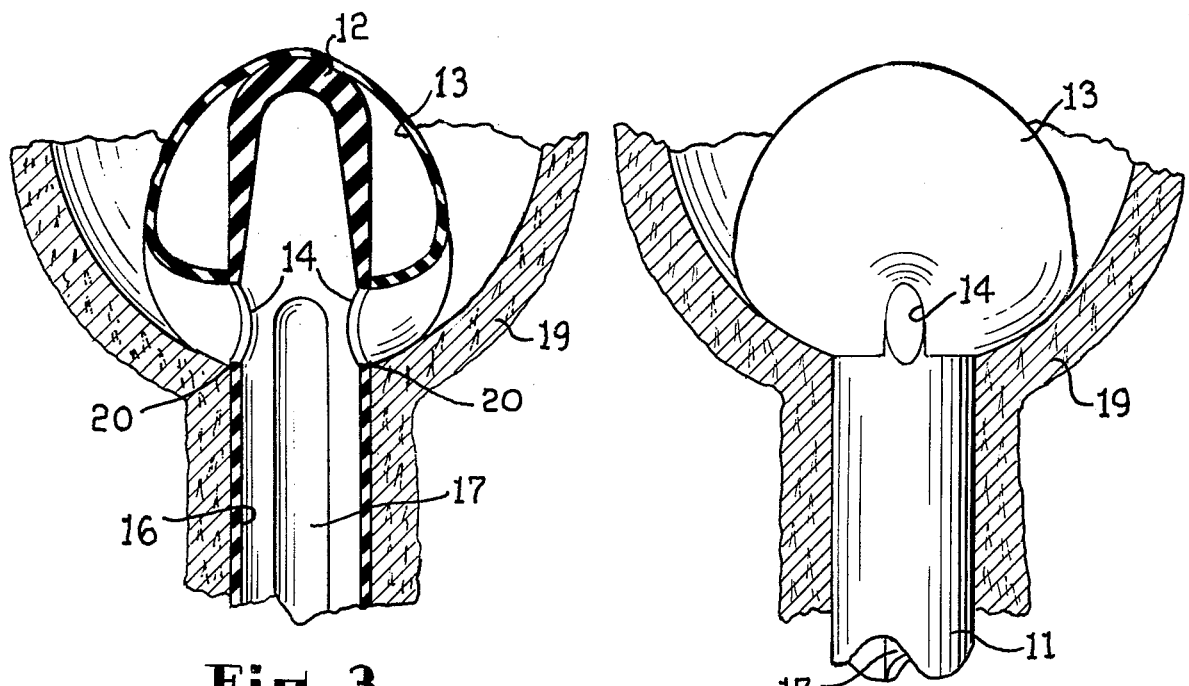
FIG. 3 is a sectional view, shown with the retention balloon inflated within a body cavity.
FIG. 4 is a front elevational view of the catheter, showing the balloon inflated within a body cavity.

Referring to FIGS. 3 and 4, the posture of the inflated balloon 13 and the drainage eyes 14 with respect to the lowermost area of the bladder 19 is illustrated. As indicated at the numeral 20 (FIG. 3), the eyes 14 are flush with the basement of the bladder, assuring complete and continuous drainage of any liquid appearing in the bladder, and effectively precluding the accumulation of the pool of liquid inherent in the use of any catheter having a balloon interposed between the drainage eye and the basement of the bladder.

As shown in FIGS. 3 and 4, the particular structural relationship of the balloon with the distal end portion of the body portion of the catheter is such that the balloon, when inflated by the admission thereto of a predetermined quantity of fluid, assumes a bilobal configuration in which a pair of opposing lobes of the balloon overlie and rest upon outwardly extending portions of the bladder basement, while those portions of the undersurface of the balloon between the lobes are indented upwardly, thereby providing unobstructed access to the drainage eyes from the bladder basement.

The construction of the catheter herein described is such as to enable the employment of a substantially errorproof method of operation. In the catheterization of a human bladder, the distal end portion of the catheter is moved through the associated urethra until the appearance of liquid at the proximal end of the catheter indicates that at least a portion of the drainage eyes have entered the bladder, and that it is safe to inflate the retention balloon without causing injury to the urethra, as might be caused with previously designed catheters having drainage eyes in a protruding tip with respect to the balloon. The movement of the catheter is then ceased, and a predetermined amount of fluid is injected into the balloon through the inflation lumen.

As the balloon distends, the pressure of the balloon lobes against the basement of the bladder moves the catheter as may be necessary to position the proximal edges of the drainage eyes at the lowest surface of the basement of the bladder.

The degree of inflation of the balloon and the associated quantity of liquid or other fluid may be predetermined by trial, if desired, before placing the catheter in service. Although the quantity of inflation fluid is not extremely critical, it is desirable, as with any other type of balloon catheter, to use the amount yielding the most advantageous placement of the catheter with respect to the cavity to be drained.

What is claimed is:

1. A flexible balloon type closed-end catheter comprising an elongate tubular body portion defining a drainage lumen, an elastic inflatable smooth-surface thimble-shaped balloon sheathed over the distal end portion of said body portion, a pair of diametrically opposed eyes apertured through the wall of said tubular body portion, said eyes being disposed adjacent to the proximal marginal portion of said thimble-shaped balloon and extending distally therebeyond, said balloon having a pair of diametrically opposed openings in registration with said eyes and said balloon being attached to the body portion at the distal tip and hermatically sealed along the proximal margin thereof to the body portion including the marginal portions along said balloon openings, and a coextensive tubular inflation lumen within said tubular body portion in communication with said balloon through an aperture in the wall of said body portion, said balloon defining a bilobate configuration in response to delivery therein of an inflation fluid through said inflation lumen, each lobe of the balloon distending symmetrically outwardly from the eyes to assure unobstructed access thereto.

2. A retention catheter comprising an elongate tubular body portion defining a drainage lumen, an elastic inflatable smooth-surface thimble-shaped balloon sheathed over the distal end of said body portion, a pair of diametrically opposed drainage eyes apertured through the wall of said body portion and extending distally beyond the proximal marginal portion of said balloon, a tubular inflation lumen coextensive with said drainage lumen in communication with said balloon through an aperture in the wall of said tubular body portion, and means effective to form a pair of indentation channels extending outwardly from said drainage eyes and inwardly along the underside of said balloon concomitant with the delivery of a predetermined quantity of fluid into said balloon, said indentation channels dividing the balloon into a pair of opposed lobes merging coextensively with the distal end of said body portion, said means including a pair of openings in said balloon extending distally from the proximal margin of said thimble-shaped balloon in registration with the drainage eyes and hermatically sealing means joining the proximal marginal portion of the balloon along the entire periphery thereof to the abutting tubular body portion.

3. The method of precluding the formation of a pool of liquid within the bladder of a human body which includes the steps of moving the balloon end portion of a balloon-type catheter through the associated urethra only until the first appearance of liquid at the proximal end of the catheter lumen, and distending an initially uninflated smooth-surfaced thimble-shaped balloon sheathed over the distal end portion of the catheter to an inflated symmetrical bilobate configuration to provide between the lobes a pair of diametrically opposed upwardly indented drainage passageways along the underside of the re-formed balloon, each passageway terminating at an associated drainage eye opening to the lumen of the catheter.

* * * * *